(12) United States Patent
Zoeller et al.

(10) Patent No.: US 6,265,618 B1
(45) Date of Patent: Jul. 24, 2001

(54) PROCESS FOR THE CONVERSION OF CARBOXYLIC ACIDS TO KETONES

(75) Inventors: Joseph Robert Zoeller, Kingsport, TN (US); Courtney Ann Crooks, Hanover, PA (US); Bruce Edwin Wilson, Midland, MI (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/615,480

(22) Filed: Jul. 13, 2000

(51) Int. Cl.$^7$ ................................................... C07C 45/29
(52) U.S. Cl. ............................................. 568/397; 568/319
(58) Field of Search ....................... 568/319, 397

(56) References Cited

U.S. PATENT DOCUMENTS 3,535,371 * 10/1970 Wolf et al. .
4,754,074   6/1988 Hussman .
5,808,148 * 9/1998 Gogate et al. .

FOREIGN PATENT DOCUMENTS 2-111722   9/1972 (DE) .
2-758113   7/1979 (DE) .
93/016419  9/1986 (JP) .

OTHER PUBLICATIONS

Yoshida et al, Catalysis Today, 28, 79–89, 1996,"Control of the structure of niobium oxide species on silica by the equilibrim absorption method".

Vedrine et al, Catalysis today, 28, 3–15, 1996 "Niobium oxide based materials as catalysts for acidic and partial oxidation type reactions ".

Weissman, Catalysis today, 28, 159–166, 1996, "Niobia–alumina supported hydroprocessing catalysts: relationship between activity and support surface acidity ".

* cited by examiner

Primary Examiner—Johann Richter
Assistant Examiner—Sikarl A. Witherspoon
(74) Attorney, Agent, or Firm—Michael J. Blake; Harry J. Gwinnell

(57) ABSTRACT

Disclosed is a process for the preparation of ketones by contacting one or more carboxylic acids with a niobium catalyst at elevated temperatures. The process includes the use of a modified base-exchanged niobium catalyst that is particularly useful for the production of cyclopropyl ketones such as cyclopropyl methyl ketone from cyclopropanecarboxylic acid and acetic acid.

18 Claims, No Drawings

PROCESS FOR THE CONVERSION OF CARBOXYLIC ACIDS TO KETONES

FIELD OF THE INVENTION

This invention pertains to a process for the preparation of ketones. More specifically, this invention pertains to the preparation of ketones by contacting one or more carboxylic acids with a niobium catalyst at elevated temperatures.

BACKGROUND OF THE INVENTION

The synthesis of ketones by contacting carboxylic acids with various metal oxide catalysts at elevated temperatures is well-known. For example, in U.S. Pat. No. 4,754,074 Hussman describes a process for the generation of dialkyl ketones using manganese dioxide supported on alumina. The Hussman patent provides an excellent overview of the prior art up to about 1988 and provides a comparison of the various prior art catalysts useful in the generation of diethyl ketone from propionic acid. Active catalysts include oxides of lead, iron, zirconium, manganese, thorium, and neodymium, with zirconium and thorium being preferred prior to Hussman's discovery of the use of manganese on alumina catalyst.

In addition to the prior art described by Hussman, several additional prior art references describe the preparation of ketones from carboxylic acids. In German Patent 2,758,113 (1979), Froelich, et al. describe the use of thorium and/or zirconium oxides with anatase ($TiO_2$) along with an optional additional support, such as alumina. German Patent 2,111,722 describes an improved process for the generation of ketones from carboxylic acids by the addition of steam to thorium oxide catalyzed processes. These processes and those described by Hussmann are conducted in the vapor phase. However, Japanese Patent 93/016419 (1983) departs from the normal vapor phase process and describes a liquid phase process using a zirconium oxide catalyst.

U.S. Pat. No. 5,808,148 (1998) discloses a process for the preparation of methacrylic acid by contacting formaldehyde and propionic acid in the presence of a niobium catalyst, preferably supported on silica. This process also produces very small amounts of diethyl ketone.

BRIEF SUMMARY OF THE INVENTION

We have discovered that catalysts comprising niobium are very efficient catalysts for the conversion of carboxylic acids to ketones, such as the generation of diethyl ketone from propionic acid. Our invention, therefore, provides a process for the preparation of a ketone by contacting at least one carboxylic acid with a niobium oxide catalyst at elevated temperatures in the substantial absence of formaldehyde. The present process is useful for the synthesis of a variety of ketones using a variety of carboxylic acids as starting material. We have found that when used in the process of this invention the catalyst is: (1) not subject to rapid deactivation, (2) most active after being operated for a number of hours, (3) demonstrates its best selectivity when operated for multiple hours, and (4) demonstrates its lowest rates immediately after reactivation. This contrasts markedly with the process in U.S. Pat. No. 5,808,148, which deactivates relatively rapidly, with a notable accompanying loss of selectivity, requiring frequent reactivation. Furthermore, the fastest rates obtained by the process of U.S. Pat. No. 5,808,148 occur immediately after reactivation.

DETAILED DESCRIPTION

The present process comprises contacting at least one carboxylic acid with a niobium catalyst at elevated temperature in the absence, or substantial absence, of formaldehyde to produce at least one ketone. When using a single carboxylic acid to produce a single ketone, the carboxylic acid contains at least one α-hydrogen atom, e.g., carboxylic acids having the general formula $$(R^1)(R^2)CHCOOH \qquad (I)$$

wherein $R^1$ and $R^2$ are selected from hydrogen, alkyl, alkenyl, cycloalkyl, carbocyclic aryl and heterocyclic aryl. In addition to carboxylic acid reactant (I), a second carboxylic acid reactant may be utilized to prepare a mixture of ketones, including an unsymmetrical ketone. The second carboxylic acid reactant may have the general formula $$R^3COOH \qquad (II)$$

wherein $R^3$ is selected from alkyl, alkenyl, cycloalkyl, and carbocyclic and heterocyclic aryl. The ketone product or products obtained from the process have the general formulas $$(R^1)(R^2)CHC(=O)CH(R^1)(R^2) \qquad (III)$$

and $$(R^1)(R^2)CHC(=O)CR^3 \qquad (IV)$$

The alkyl radicals which $R^1$, $R^2$ and $R^3$ may represent may be unbranched or branched, unsubstituted or substituted alkyl containing up to about 20 carbon atoms. Example of the substituents which may be present on the alkyl radicals include alkoxy, e.g. $C_1$ to $C_4$ alkoxy; halogen, e.g., chloro and bromo; and aryl, e.g., phenyl and tolyl. The alkyl radicals preferably contain up to 12 carbon atoms, and most preferably are unsubstituted alkyl containing up to about 6 carbon atoms. The alkenyl radicals which $R^1$, $R^2$ and $R^3$ may represent also may be unbranched or branched, unsubstituted or substituted alkenyl containing up to about 20 carbon atoms. The cycloalkyl radicals may contain 5 to 7 ring carbon atoms and may be substituted with alkyl, e.g., $C_1$ to $C_4$ alkyl; alkoxy, e.g., $C_1$ to $C_4$ alkoxy; and/or halogen, e.g., chloro and bromo. The aryl radicals which $R^1$, $R^2$ and $R^3$ may represent may contains up to about 10 carbon atoms such as phenyl; phenyl substituted with alkyl, e.g., $C_1$ to $C_4$ alkyl; alkoxy, e.g., $C_1$ to $C_4$ alkoxy; and/or halogen, e.g., chloro and bromo; naphthyl; and naphthyl substituted with alkyl, e.g., $C_1$ to $C_4$ alkyl; alkoxy, e.g., C: to $C_4$ alkoxy; and/or halogen, e.g., chloro and bromo. Carboxylic acid reactant (I) preferably contains at least two α-hydrogen atoms, i.e., $R^2$ preferably is hydrogen. The reactant employed in the present process consists essentially of one or more carboxylic acids, i.e., the process is carried our in the absence of any amount of formaldehyde which would interfere with the production of ketone products. It will be apparent to those skilled in the art that the radicals represented by $(R^1)(R^2)CH$ and $R^3$ may be the same or different.

The niobium catalyst used to effect the transformation of the carboxylic acids to ketones according to the present invention may be unsupported niobium oxide or, preferably, in the form of a supported catalyst comprising niobium oxide supported on a catalyst support material such as silica, alumina, and titania. These catalysts are well known and may be prepared by conventional techniques. For example, the generation of niobium-silica catalysts using a co-precipitation of silica and niobium oxide is described in U.S. Pat. No. 5,808,148 while an impregnation technique is described in H. Yoshida, T. Tanaka, T. Yoshida, T. Funabiki, and S. Yoshida, *Catalysis Today*, 28, 79 (1996). Further, in J. C. Vedrine, G. Coudurier, A. Ouqour, P. G. Pries de Oliveira, and J. C. Volta, *Catalysis Today*, 28, 3 (1996), methods for the generation of niobium-alumina catalysts as well as methods for the generation of pure niobium oxide are described. Alternatively, impregnation techniques for the generation of niobium oxide on alumina are described in J. G. Weissman, *Catalysis Today*, 28, 3 (1996). The catalytically active niobium is believed to be present primarily as $Nb_2O_5$ although other known oxides such as $Nb_2O_3$ and $NbO_2$ may be present.

The amount of niobium in or on the catalysts useful in the present invention may vary from 1 weight percent Nb on supported catalysts to 70 weight percent niobium in the case of pure niobium (V) oxide. The preferred supported catalysts comprise about 5 to 35 weight percent niobium, based on the total weight of the catalyst, deposited on a catalyst support material such as silica, alumina, and titania. Silica is the preferred catalyst support.

The activity and/or selectivity of the above described, niobium catalysts may be enhanced by contacting the above catalysts with an inorganic basic compound to obtain a base-exchanged, niobium catalyst. Such base-exchanged, niobium catalysts are especially advantageous when the carboxylic acid feedstock or ketone product contains one or more groups sensitive to the conditions employed in the ketone-forming process. For example, in the synthesis of cyclopropyl ketones from cyclopropanecarboxylic acid and another carboxylic acid, e.g., an alkanoic acid, the cyclopropanecarboxylic acid feedstock is sensitive to acid and tends to undergo a competitive rearrangement to (-butyrolactone. The synthesis of cyclopropyl methyl ketone from cyclopropanecarboxylic acid and acetic is exemplary of the benefits provided by the use of a base-exchanged, niobium catalyst. When using an unexchanged (unmodified) niobium catalyst, the mole ratio of cyclopropyl methyl ketone to (-butyrolactone is 1:1. However, when a base-exchanged, e.g., potassium-exchanged, niobium catalyst is used, the mole ratio of cyclopropyl methyl ketone to (-butyrolactone is 3:1. Furthermore, the rate of formation of cyclopropyl methyl ketone using a potassium-exchanged, niobium catalyst has been found to be more than five times the rate of formation when using an unexchanged niobium catalyst under otherwise identical conditions.

The base-exchanged, niobium catalysts preferably are alkali metal-exchanged, niobium catalysts, most preferably potassium-exchanged, niobium catalysts. The base-exchanged (or base-modified), niobium catalysts may be prepared by contacting the above-described, niobium catalysts, e.g., either unsupported or supported niobium oxide, with an aqueous solution of a base such as an alkali metal or alkaline earth metal hydroxide, carbonate and/or bicarbonate. Such contacting typically comprises mixing the unexchanged, niobium catalyst with an aqueous solution containing about 0.1 to 50 weight percent, preferably about 1 to 20 weight percent, of an alkali metal or alkaline earth metal hydroxide, carbonate and/or bicarbonate, preferably an alkali hydroxide such as potassium hydroxide. The base-exchanging or modifying procedure may be carried out at a temperature of about −10 to 100° C., typically at approximately ambient temperature, for up to about 24 hours, typically from about 5 minutes to 4 hours. At the conclusion of the base-exchanging period, the catalyst is separated from the solution of base and washed with water. The base exchanged catalyst normally is calcined by heating at a temperature of about 250 to 800° C. for a period of up to about 48 hours, typically from about 4 to 8 hours, in the presence of an oxygen-containing gas such as air.

The use of the above-described base-exchanged catalysts in the synthesis of cyclopropyl alkyl ketones constitutes a preferred embodiment of the present invention. In this embodiment, cyclopropanecarboxylic acid and an alkanoic acid, e.g., an aliphatic, carboxylic acid, containing up to about 12 carbon atoms, preferably 2 to 6 carbon atoms, are contacted in the presence of a base-exchanged, niobium catalyst at elevated temperatures in the substantial absence of formaldehyde to produce a cyclopropyl alkyl ketone.

The process may be operated over a wide range of temperatures and pressures. The elevated temperature normally is within the range of about 200 to 550° C., preferably in the range of about 300 to 450° C. At these temperatures, most of the carboxylic acids are vaporized at atmospheric pressure. In a preferred mode of operation, the carboxylic acid or acids are vaporized prior to contact with the catalyst. Optionally, the vapor may be added along with an inert (non-reactive) diluent gas such as nitrogen, helium, argon, methane, or carbon dioxide. Although not preferred, the process may be carried out in the liquid phase by employing supraatmospheric pressure as necessary to maintain the carboxylic acid(s) reactant(s) as liquids.

Since the preferred operation is in the vapor phase, the preferred pressure ranges will be chosen to maintain the carboxylic acid components above their dew point. However, the dew point is a complex function of the nature of the carboxylic acid(s) being used, the pressure, and the concentration of diluent gases if they are used in the operation. The operational pressures typically are in the range of 0.01 to 30 bar absolute (bara), with pressures of 0.1 to 5 bara being preferred.

The gaseous flow rates used in the preferred vapor phase operation of the process may vary widely with the preferred gaseous flow rates being a matter of empirical optimization for each individual carboxylic acid or combination of carboxylic acids. Typically, the gas flow rates are in the range of 10 to 10,000 liters per kg catalyst per hour with a range of 50–1000 liters per kg catalyst per hour being preferred.

The catalyst is most effective when the process is operated continuously, without interruption of the feeds or reactivation. However, if after long periods of time, reactivation becomes necessary, it can be accomplished by common means, although reactivation with small amounts of oxygen is preferred.

The process provided by the present invention is further illustrated by the following examples. The percentages given in the examples are by weight unless otherwise specified.

Preparation of Catalyst A

A 20% niobium oxide on silica catalyst was prepared by a modification of the process described in U.S. Pat. No. 5,808,148. With constant stirring, 9.684 g ammonium hexafluoroniobate (V) was dissolved in 64.5 mL of distilled water. This solution was added to an evaporating dish, along with 64.65 g colloidal $SiO_2$ solution (36% silica in water, NALCO colloidal silica 1034-A.) This mixture was heated with stirring until apparently dry and free flowing. Once the mixture was dry, quartz wool was placed in the bottom of a quartz reactor tube and the mixture was then added to the tubular quartz reactor. Under a continuous flow of air (added at the rate of 50 standard cc per minute), the mixture was calcined at 300° C. for four hours, and then at 450° C. for six hours. The reactor was cooled and the material in the reactor was collected. (Some material was found beyond the quartz wool plug and was discarded.) The calcined catalyst was crushed using a mortar and pestle, and sieved using one screen of 14 mesh followed by another screen of 20 mesh. In this manner, 13 g of 14–20 mesh catalyst used as the desired 20%$Nb_2O_5$ on silica catalyst was obtained. In addition, there was 16 g of fine mesh material obtained.

Preparation of Catalyst B

A slurry of 22 grams of 14–20 mesh of a catalyst consisting of 20 weight percent $Nb_2O_5$ on $SiO_2$, prepared using the procedure described above for Catalyst A, was stirred with 22 grams of 5 weight percent aqueous KOH for 10–15 minutes and the mixture filtered through a frittered glass filter. The filtrate was washed with 100–200 mL of distilled water and dried on the filter. Once the mixture was dry, quartz wool was placed in the bottom of a quartz reactor tube and the mixture was then added to the tubular quartz reactor. Under a continuous flow of air (added at the rate of 50 standard cc per minute), the mixture was calcined at 300° C. for four hours, and then at 450° C. for six hours. The reactor was cooled and the material in the reactor was collected. The base-exchanged, niobium catalyst thus prepared was sieved as described above. Most of the material retained the 14–20 mesh size.

General Procedure for the Conversion of Carboxylic Acids to Ketones

The following general procedure was used for the conversion of a carboxylic acid or a mixture of carboxylic acids to ketones. The apparatus consisted of a vertically mounted reactor system consisting of a reactor head (at the top), followed sequentially by a quartz reaction tube, a condenser, and a collection vessel. The quartz reactor tube was placed in a vertically mounted electric furnace.

The reactor head was constructed using five ground glass joints arranged around a glass sphere of roughly 100 cc. At the top of the reactor head were three standard taper female ground glass joints. The center joint was constructed from a 14/35 standard taper female ground glass joint which would accept a 14/35 standard taper ground glass thermal well. To each side of this 14/35 standard taper center joint was placed two 10/30 female standard taper ground glass joints connected to a bent drip tip. The first 10/30 standard taper ground glass joint was fitted with a septum which was connected to the carboxylic acid feed by piercing the septum and pushing a chemically inert feed line through the septum. The second 10/30 standard taper ground glass joint was not used in these experiments and was plugged with a standard taper ground glass 10/30 stopper. Mounted at a 45° C. angle to these three female joints, was a male 24/29 standard taper ground glass joint (referred to hereafter as the side-arm), which would be used to both fill the reactor with catalyst during assembly and to feed nitrogen when operating the reactor. At the base of the reactor, and carefully aligned with the 14/35 standard taper ground glass joint to be used for the thermal well, was a 24/29 female standard taper joint. Each joint was fitted with a "hook" to allow a spring to be connected if needed to keep the assembly from leaking.

The reactor consisted of a 43-cm long quartz tube with a diameter of 2.5 cm (1 inch) which had been fitted with a 29/26 standard taper male ground glass joint at the top and a 24/40 male standard taper ground glass joint at the bottom. Four indentations were placed at a height of 10 cm above the 24/40 standard taper male ground glass joint.

To assemble the reactor, a thermal well with a 14/35 standard taper male ground glass joint located 2.54 cm (1 inch) from the top of the tube and measuring 38.5 cm in length and having a diameter of 1 cm was placed in the center joint of the reactor head. A 20 mm outside diameter glass crown was inserted into a tubular quartz reactor, followed by a small quartz wool plug (secure, but not tightly packed.) The reactor head and thermal well were placed on top of the tubular reactor. Through the 45° mounted side arm, quartz chips were added until they were level with the bottom of the thermal well. This was followed by 9.6 mL (4 grams) of the 14–20 mesh 20% niobium oxide on silica catalyst prepared as described above. Finally, the remaining void volume in the reactor section was filled with additional quartz chips.

The reactor was supported in a hood and the reactor zone placed in an electrically heated furnace. The feed tube was inserted in the septum and the 45° mounted side arm was attached to a nitrogen inlet which consisted of a standard taper 24/24 standard taper female glass joint with a glass to Swagelock® adapter which was then connected to the nitrogen feed.

The condenser was a West condenser, which had been modified by placing indentations near the base of the cooling section, and had a 28/15 ground glass female ball joint at the top and a standard taper 24/40 joint at the base. The condenser was filled with 7 mm by 7 mm glass Rasching rings. (The indentations were sufficiently deep to hold the Rasching rings in place.) The condenser was water cooled and attached to the reactor using an adapter with a 24/40 standard taper female ground glass joint at the top and a 28/15 ground glass male ball joint at the base.

This condenser was attached to a vacuum adapter (actually used as a gas outlet in this application) with hose connector with 24/40 standard taper joints. The collection vessel was a standard 250 mL 24/40 round bottom flask which had been fitted with a Teflon stopcock at the bottom to allow sample collection and removal. Using Tygon® tubing, the hose connection on the vacuum was attached sequentially to a 50 mL gas collection tube (with 2 stopcocks) followed by a double gas bubbler.

Three thermocouples were then inserted into the thermal well, with lengths corresponding to the top, middle, and bottom of the catalyst bed. The furnace was operated to maintain a constant temperature of 380° C. at the bottom of the catalyst bed throughout the experiment and the nitrogen flow set at 40 mL/minute (0.0981 mol/hour) throughout the experiment. The water condenser was turned on and the carboxylic acid feed was introduced through the septum on the reactor head at a rate of 0.25 mL/minute once the temperature stabilized. Control of the feed rates was achieved using a Tylan® flow controller for the nitrogen feed and an Alltech® HPLC pump to regulate the liquid feed rates. The temperature was sufficient to vaporize the carboxylic acid, and the continuous nitrogen flow moved the vapor through the apparatus.

Liquid and gas samples were collected at variable intervals. The liquid product was obtained by draining the collection vessel into a preweighed sample bottle. The weight of each sample was recorded and each sample was subsequently analyzed by gas chromatography (GC) using an internal standard method. Similarly, the gas sample was obtained by turning the stopcocks on the gas collection vessel, removing the gas collection vessel and replacing it with a new gas collection vessel. The gas sample was subsequently analyzed by GC as well. The liquid product was analyzed for the ketone product and carboxylic acid reactants, while the gaseous effluent was analyzed for C-1 through C-3 hydrocarbons, carbon monoxide, carbon dioxide, nitrogen, and oxygen. (Each gas sample was normalized for air contamination during sampling and analysis using the oxygen analysis.)

The mass and molar quantities of each component (i) in the liquid product samples was calculated as follows:

$Mass_i$=(Weight % by GC/100)·weight sample $Moles_i$=$Mass_i$/ Molecular weight$_i$ Further, the production rates (space time yields) for the desired ketones could be calculated as follows:

Space time yield =$Mass_i$/(catalyst volume·sample interval)

Molar space time yield =$Moles_i$/(catalyst volume·sample interval)

Due to the nature of the sampling, the gas analyses are a less accurate, but the molar quantities of the gas by-products could be estimated using the formula:

$$\text{Molar space time yield for } gas_i = \frac{\text{molar nitrogen flow rate} \times \% \, gas_i}{\text{corrected \% nitrogen in sample}}$$

wherein the corrected % nitrogen in sample is equal to the % nitrogen measured-(3.728×% oxygen in sample). The corrected % nitrogen in sample is intended to correct for air introduced in the course of sampling and analysis.

EXAMPLE 1

Conversion of Propionic Acid to Diethyl Ketone

Using Catalyst A and the general procedure described above, propionic acid was fed at a rate of 0.25 mL/minute (0.201 mol/hour) over a period of 94.03 hours. Samples were removed at alternating intervals of approximately 8 and 16 hours. The operation and sampling times (hours), sample weights (g), and GC analyses of the liquid samples are summarized in Table I.

TABLE I

| Liquid Sample Number | Time of Operation | Interval Between Samples | Sample Weight | Percent Diethyl Ketone | Percent Propionic Acid |
|---|---|---|---|---|---|
| 1 | 8.17 | 8.17 | 106.85 | 19 | 79 |
| 2 | 23.17 | 15.00 | 198.98 | 26 | 72 |
| 3 | 31.63 | 8.47 | 111.49 | 30 | 70 |
| 4 | 46.70 | 15.07 | 181.29 | 31 | 69 |
| 5 | 54.70 | 8.00 | 103.17 | 30 | 68 |
| 6 | 70.70 | 16.00 | 204.62 | 30 | 67 |
| 7 | 78.95 | 8.25 | 112.98 | 29 | 66 |
| 8 | 94.03 | 15.08 | 197.66 | 30 | 68 |

No other liquid by-products were detected by GC other than the small trace of isobutyric acid contaminant present in the propionic acid feed. Analyses of the gas samples revealed the presence of carbon dioxide, carbon monoxide and ethane. The diethyl ketone production rate ranged from 3.1 moles per liter of catalyst per hour for the first 8.17 hours of operation to 4.9 moles per liter of catalyst per hour for the 8.25 hours of operation from hour of operation 70.7 to hour 78.95. Over the course of the reaction, which ran for 94.03 hours, a total of 4.03 moles (347 g) of diethyl ketone were obtained giving an overall space time yield of 4.5 mole per liter of catalyst per hour (380 grams per liter of catalyst per hour). The selectivity to diethyl ketone was >99%.

EXAMPLE 2

Conversion of Benzoic Acid and Acetic Acid to Acetophenone

Using Catalyst A and the general procedure described above, a solution of 22.2% benzoic acid in acetic acid was added at a rate of 0.25 mL/minute, corresponding to an addition rate of 0.029 mol/hour benzoic acid and 0.204 mol/hour of acetic acid. The process was operated for a total of 24 hours with liquid and gas samples taken approximately every two hours. The liquid samples were analyzed for benzoic acid, acetic acid, acetophenone, and acetone. Result for these analyses appear below. The sampling times (hours), sample weights, (grams) and GC analyses are summarized in Table II. Over the 24.2 hours of the experiment a total of 0.693 moles of benzoic acid of which 0.452 moles were recovered as unconverted benzoic acid and 0.177 moles were converted to acetophenone. This represents a 35% conversion of benzoic acid with a 79% selectivity to acetophenone. The average production rate was 0.76 mole per liter of catalyst per hour.

TABLE II

| Liquid Sample Number | Time of Operation | Interval Between Samples | Sample Weight | Percent Benzoic Acid | Percent Acetic Acid | Percent Acetophenone | Percent Acetone |
|---|---|---|---|---|---|---|---|
| 1 | 2.0 | 2.0 | 17.28 | 14.8 | 74 | 5.1 | 3.1 |
| 2 | 4.0 | 2.0 | 29.73 | 15.8 | 74 | 5.9 | 3.0 |
| 3 | 6.0 | 2.0 | 30.42 | 16.6 | 72 | 5.9 | 3.2 |
| 4 | 8.0 | 2.0 | 27.90 | 15.7 | 72 | 6.3 | 3.4 |
| 5 | 10.0 | 2.0 | 30.50 | 16.2 | 71 | 5.9 | 3.0 |
| 6 | 12.0 | 2.0 | 31.10 | 15.7 | 73 | 5.6 | 3.1 |
| 7 | 14.0 | 2.0 | 27.03 | 16.3 | 71 | 7.3 | 4.3 |
| 8 | 16.1 | 2.1 | 31.31 | 15.9 | 72 | 6.7 | 3.8 |
| 9 | 18.1 | 2.0 | 29.83 | 16.3 | 70 | 6.4 | 3.7 |
| 10 | 20.2 | 2.1 | 28.83 | 14.6 | 71 | 6.7 | 4.0 |
| 11 | 22.2 | 2.0 | 30.47 | 16.3 | 73 | 6.1 | 3.8 |
| 12 | 24.2 | 2.0 | 31.26 | 16.5 | 71 | 5.8 | 3.6 |

EXAMPLE 3

Conversion of Hexanoic Acid to 6-Undecanone

Using Catalyst A and the general procedure described above, hexanoic acid was contacted with the supported niobium oxide catalyst using a feed rate of 0.25 mL/minute (0.12 mol/hour) and a total feed time of three hours. A total of 35.23 g of product was collected. Analysis of the recovered product showed that 5.6 g (33 mmol) of 6-undecanone formed over the course of the three hour experiment. This corresponds to a production rate of 1.14 moles per liter catalyst per hour.

EXAMPLE 4

Conversion of Hexanoic Acid and Acetic Acid to a Mixture of Acetone, 2-Heptanone and 6-Undecanone Using catalyst A and the general procedure described above, a solution of 1:1 molar ratio hexanoic acid:acetic acid (hexanoic acid:acetic acid weight ratio =1.93) was added at a rate of 0.25 mL/minute, corresponding to an addition rate of 0.0757 mol/hour for each carboxylic acid reactant. The process was operated for a total of 4.85 hours with liquid and gas samples taken approximately every 1.5 hours. The liquid samples were analyzed for acetic acid, hexanoic acid, 6-undecanone, 2-heptanone, and acetone. The results of these analyses appear in Table III. Over the course of the experiment, 34.6 mmol (4.0 g) of 2-heptanone and 16.6 mmol (2.8 g) of 6-undecanone were formed at rates of 0.74 moles per liter of catalyst per hour and 0.36 moles per liter of catalyst per hour, respectively. In addition, 11.7 mmol of acetone were recovered, representing a production rate of 0.25 moles per liter of catalyst per hour.

EXAMPLE 5

Cyclopropyl methyl ketone (CPMK) was prepared from cyclopropanecarboxylic acid (CPCA) and acetic acid using Catalyst A and the general procedure except that the temperature at the base of the reactor was maintained at 360° C. A solution of 2:1 molar ratio of acetic acid and cyclopropanecarboxylic acid (acetic acid:CPCA mole ratio =2:1; weight ratio =1.4:1) was added at a rate of 0.25 mL/minute, corresponding to an addition rate of 0.0772 mol/hour for CPCA and 0.155 mol/hour for acetic acid. The process was operated for a total of 24 hours with liquid and gas samples taken approximately every 2 hours. The liquid samples were analyzed for acetic acid, CPCA, CPMK, acetone, and γ-butyrolactone (GBL). The results of these analyses appear in Table IV. Over the course of the experiment, 41.1 mmol (3.45 g) of CPMK and 40.3 mmol (3.46 g) of GBL were formed at rates of 0.18 moles per liter of catalyst per hour and 0.17 moles per liter of catalyst per hour, respectively. In addition, 68.0 mmol of acetone were recovered, representing a production rate of 0.30 moles per liter of catalyst per hour.

TABLE III

| Liquid Sample Number | Time of Operation | Interval Between Samples | Sample Weight | Percent Hexanoic Acid | Percent Acetic Acid | Percent 2-Heptanone | Percent 2-Undecanone | Percent Acetone |
|---|---|---|---|---|---|---|---|---|
| 1 | 1.5 | 1.5 | 19.70 | 45.8 | 36.6 | 6.2 | 3.9 | 1.30 |
| 2 | 3.35 | 1.85 | 20.78 | 58.7 | 29.8 | 7.3 | 5.5 | 1.14 |
| 3 | 4.85 | 1.5 | 21.02 | 54.6 | 25.6 | 5.8 | 4.4 | 0.88 |

TABLE IV

| Liquid Sample Number | Time of Operation | Interval Between Samples | Sample Weight | Percent CPCA | Percent Acetic Acid | Percent CPMK | Percent GBL | Percent Acetone |
|---|---|---|---|---|---|---|---|---|
| 1 | 2.0 | 2.0 | 29.24 | 51.9 | 47.2 | 0.83 | 1.42 | 0.41 |
| 2 | 4.0 | 2.0 | 31.56 | 49.0 | 48.1 | 1.29 | 1.50 | 0.75 |
| 3 | 6.0 | 2.0 | 32.34 | 47.1 | 50.3 | 1.10 | 1.15 | 0.68 |
| 4 | 8.0 | 2.0 | 31.64 | 44.5 | 53.1 | 1.01 | 1.04 | 0.71 |
| 5 | 10.0 | 2.0 | 30.25 | 39.6 | 58.2 | 1.07 | 1.07 | 0.98 |
| 6 | 12.0 | 2.0 | 31.19 | 36.1 | 61.8 | 0.95 | 0.89 | 1.01 |
| 7 | 14.0 | 2.0 | 31.80 | 32.1 | 65.7 | 0.84 | 0.76 | 1.04 |
| 8 | 16.0 | 2.0 | 31.54 | 28.2 | 69.1 | 0.77 | 0.66 | 1.08 |
| 9 | 18.0 | 2.0 | 34.81 | 24.5 | 73.6 | 0.85 | 0.70 | 1.56 |
| 10 | 20.0 | 2.0 | 26.69 | 23.5 | 75.2 | 0.76 | 0.60 | 1.44 |
| 11 | 22.0 | 2.0 | 29.49 | 23.5 | 75.6 | 0.74 | 0.58 | 1.32 |
| 12 | 24.0 | 2.0 | 36.60 | 23.9 | 75.1 | 0.78 | 0.70 | 1.51 |

EXAMPLE 6

Cyclopropyl methyl ketone (CPMK) was prepared from cyclopropanecarboxylic acid (CPCA) and acetic acid using Catalyst B and the general procedure except that the temperature at the base of the reactor was maintained at 360° C. A solution of 2:1 molar ratio of acetic acid and cyclopropanecarboxylic acid (acetic acid:CPCA mole ratio =2:1; weight ratio =1.4:1) was added at a rate of 0.25 mL/minute, corresponding to an addition rate of 0.0772 mol/hour for CPCA and 0.155 mol/hour for acetic acid. The process was operated for a total of 30.17 hours with liquid and gas samples taken approximately every 2 hours. The liquid samples were analyzed for acetic acid, CPCA, CPMK, acetone, and γ-butyrolactone (GBL). The results of these analyses appear in Table V. Over the course of the experiment, 268.7 mmol (22.57 g) of CPMK and 87.4 mmol (7.51 g) of GBL were formed at rates of 0.93 moles per liter of catalyst per hour and 0.30 moles per liter of catalyst per hour, respectively. In addition, 365.6 mmol of acetone were recovered, representing a production rate of 1.26 moles per liter of catalyst per hour.

This example illustrates that the optional base-exchanged niobium oxide catalysts can yield superior results and selectivity. Although the rates to all products are accelerated by the base-exchange modification of the niobium catalyst, the rate acceleration leading the condensation products, CPMK and acetone, is much more pronounced than the acceleration toward GBL.

TABLE V

| Liquid Sample Number | Time of Operation | Interval Between Samples | Sample Weight | Percent CPCA | Percent Acetic Acid | Percent CPMK | Percent GBL | Percent Acetone |
|---|---|---|---|---|---|---|---|---|
| 1 | 2.00 | 2.00 | 20.58 | 40.6 | 54.8 | 2.39 | 1.05 | 2.46 |
| 2 | 4.08 | 2.08 | 30.96 | 39.7 | 51.3 | 3.96 | 1.49 | 3.95 |
| 3 | 6.08 | 2.00 | 29.97 | 39.4 | 49.7 | 4.73 | 1.69 | 4.60 |
| 4 | 8.00 | 2.00 | 31.15 | 38.9 | 48.9 | 5.14 | 1.69 | 4.88 |
| 5 | 10.08 | 2.00 | 29.79 | 39.0 | 49.5 | 5.11 | 1.75 | 4.92 |
| 6 | 12.08 | 2.00 | 30.64 | 39.0 | 48.8 | 5.28 | 1.74 | 4.96 |
| 7 | 14.08 | 2.00 | 30.27 | 39.1 | 49.0 | 5.40 | 1.73 | 5.16 |
| 8 | 16.08 | 2.00 | 29.83 | 38.9 | 49.2 | 5.49 | 1.73 | 5.26 |
| 9 | 18.08 | 2.00 | 29.65 | 39.0 | 49.0 | 5.22 | 1.77 | 4.90 |
| 10 | 20.08 | 2.00 | 28.54 | 38.8 | 48.9 | 5.38 | 1.71 | 4.98 |
| 11 | 22.08 | 2.00 | 32.40 | 38.6 | 48.6 | 5.37 | 1.71 | 4.90 |
| 12 | 24.08 | 2.00 | 30.29 | 38.5 | 48.6 | 5.43 | 1.72 | 5.02 |
| 13 | 26.08 | 2.00 | 28.93 | 39.6 | 48.4 | 5.31 | 1.83 | 4.76 |
| 14 | 28.08 | 2.00 | 30.09 | 39.2 | 47.8 | 5.62 | 1.83 | 5.02 |
| 15 | 30.17 | 2.08 | 32.00 | 38.3 | 49.3 | 5.50 | 1.73 | 5.09 |

The invention has been described in detail with particular reference to preferred embodiments thereof, but it will be understood that variations and modifications can be effected within the spirit and scope of the invention.

We claim:

1. Process for the preparation of a ketone which comprises contacting at least one carboxylic acid with a niobium oxide catalyst at elevated temperature in the substantial absence of formaldehyde.

2. Process according to claim 1 which comprises contacting at least one carboxylic acid selected from carboxylic acids having the formula $$(R^1)(R^2)CHCOOH \tag{I}$$

or a mixture of carboxylic acids having formulas (I) and $$R^3COOH \tag{II}$$

wherein $R^1$ and $R^2$ are selected from hydrogen, alkyl, alkenyl, cycloalkyl, and carbocyclic and heterocyclic aryl; $R^3$ is selected from alkyl, alkenyl, cycloalkyl, and carbocyclic and heterocyclic aryl; and the process is operated at a temperature of about 200 to 550° C.

3. Process for the preparation of a ketone which comprises contacting at least one carboxylic acid selected from carboxylic acids having the formula $$(R^1)(R^2)CHCOOH \quad (I)$$

or a mixture of carboxylic acids having formulas (I) and $$R^3COOH \quad (II)$$

with a supported niobium oxide catalyst at a temperature of about 350 to 450° C. in the substantial absence of formaldehyde, wherein $R^1$ and $R^2$ are selected from alkyl radicals containing up to 12 carbon atoms; and $R^3$ is selected from alkyl radicals containing up to 12 carbon atoms and phenyl.

4. Process according to claim 3 wherein the supported niobium oxide catalyst comprises about 5 to 35 weight percent niobium deposited on a catalyst supported material selected from silica, alumina and titania.

5. Process for the preparation of a ketone which comprises contacting at least one carboxylic acid selected from carboxylic acids having the formula $$(R^1)(R^2)CHCOOH \quad (I)$$

or a mixture of carboxylic acids having formulas (I) and $$R^3COOH \quad (II)$$

with a supported niobium oxide catalyst comprising about 5 to 35 weight percent niobium deposited on a catalyst supported material selected from silica, alumina and titania at a temperature of about 300 to 450° C. in the substantial absence of formaldehyde, wherein $R^1$ is selected from alkyl containing up to 6 carbon atoms; and $R^2$ is hydrogen; and $R^3$ is selected from alkyl containing up to 6 carbon atoms and phenyl.

6. Process according to claim 5 wherein the supported niobium oxide catalyst comprises about 5 to 35 weight percent niobium deposited silica.

7. Process for the preparation of a ketone which comprises contacting at least one carboxylic acid with a base-exchanged, niobium oxide catalyst at elevated temperature in the substantial absence of formaldehyde.

8. Process according to claim 7 which comprises contacting at least one carboxylic acid selected from carboxylic acids having the formula $$(R^1)(R^2)CHCOOH \quad (I)$$

or a mixture of carboxylic acids having formulas (I) and $$R^3COOH \quad (II)$$

wherein $R^1$ and $R^2$ are selected from hydrogen, alkyl, alkenyl, cycloalkyl, and carbocyclic and heterocyclic aryl; $R^3$ is selected from alkyl, alkenyl, cycloalkyl, and carbocyclic and heterocyclic aryl; and the process is operated at a temperature of about 200 to 550° C.

9. Process for the preparation of a ketone which comprises contacting at least one carboxylic acid selected from carboxylic acids having the formula $$(R^1)(R^2)CHCOOH \quad (I)$$

or a mixture of carboxylic acids having formulas (I) and $$R^3COOH \quad (II)$$

with a base-exchanged, supported niobium oxide catalyst at a temperature of about 300 to 450° C. in the substantial absence of formaldehyde, wherein $R^1$ and $R^2$ are selected from alkyl radicals containing up to 12 carbon atoms; and $R^3$ is selected from alkyl radicals containing up to 12 carbon atoms and phenyl.

10. Process according to claim 9 wherein the catalyst is an alkali-exchanged, supported niobium oxide catalyst comprising about 5 to 35 weight percent niobium deposited on a catalyst supported material selected from silica, alumina and titania.

11. Process for the preparation of a ketone which comprises contacting at least one carboxylic acid selected from carboxylic acids having the formula $$(R^1)(R^2)CHCOOH \quad (I)$$

or a mixture of carboxylic acids having formulas (I) and $$R^3COOH \quad (II)$$

with a potassium-exchanged, supported niobium oxide catalyst comprising about 5 to 35 weight percent niobium deposited on a catalyst supported material selected from silica, alumina and titania at a temperature of about 300 to 450° C. g in the substantial absence of formaldehyde, wherein $R^1$ is selected from alkyl containing up to 6 carbon atoms; and $R^2$ is hydrogen; and $R^3$ is selected from alkyl containing up to 6 carbon atoms and phenyl.

12. Process according to claim 11 wherein the potassium-exchanged, supported niobium oxide catalyst comprises about 5 to 35 weight percent niobium deposited silica.

13. Process for the preparation of a cyclopropyl alkyl ketone which comprises contacting cyclopropanecarboxylic acid and an alkanoic acid containing up to about 12 carbon atoms with a base-exchanged, niobium oxide catalyst at elevated temperature in the substantial absence of formaldehyde.

14. Process according to claim 13 wherein the alkanoic acid contains 2 to 6 carbon atoms and the process is operated at a temperature of about 200 to 550° C.

15. Process for the preparation of a cyclopropyl alkyl ketone which comprises contacting cyclopropylcarboxylic acid and an alkanoic acid containing 2 to 6 carbon atoms with a base-exchanged, supported niobium oxide catalyst at a temperature of about 350 to 450° C. in the substantial absence of formaldehyde.

16. Process according to claim 15 wherein the catalyst is an alkali-exchanged, supported niobium oxide catalyst comprising about 5 to 35 weight percent niobium deposited on a catalyst supported material selected from silica, alumina and titania.

17. Process for the preparation of a cyclopropyl alkyl ketone which comprises contacting cyclopropanecarboxylic acid and an alkanoic acid containing 2 to 6 carbon atoms with a potassium-exchanged, supported niobium oxide catalyst comprising about 5 to 35 weight percent niobium deposited on a catalyst supported material selected from silica, alumina and titania at a temperature of about 300 to 450° C. in the substantial absence of formaldehyde.

18. Process according to claim 17 wherein the potassium-exchanged, supported niobium oxide catalyst comprises about 5 to 35 weight percent niobium deposited silica.

* * * * *